(12) United States Patent  
Hoffman et al.

(10) Patent No.: US 8,372,140 B2  
(45) Date of Patent: Feb. 12, 2013

(54) IMPLANTABLE VALVE PROSTHESIS WITH INDEPENDENT FRAME ELEMENTS

(75) Inventors: Grant T. Hoffman, Bloomington, IN (US); Sean D. Chambers, Bloomington, IN (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 300 days.

(21) Appl. No.: 12/683,670

(22) Filed: Jan. 7, 2010

(65) Prior Publication Data

US 2010/0174364 A1 Jul. 8, 2010

Related U.S. Application Data

(60) Provisional application No. 61/142,940, filed on Jan. 7, 2009.

(51) Int. Cl.
A61F 2/06 (2006.01)

(52) U.S. Cl. ............ 623/1.26; 623/1.13; 623/1.24; 623/2.17; 623/2.18

(58) Field of Classification Search ............ 623/1.24, 623/1.3, 2.17, 1.13, 1.26, 2.18
See application file for complete search history.

(56) References Cited

U.S. PATENT DOCUMENTS

| | | | |
|---|---|---|---|
| 5,500,014 A | 3/1996 | Quijano et al. | |
| 5,607,465 A * | 3/1997 | Camilli | 623/1.24 |
| 5,851,232 A | 12/1998 | Lois | |
| 6,036,725 A * | 3/2000 | Avellanet | 623/1.13 |
| 6,287,330 B1 | 9/2001 | Johansson et al. | |
| 6,287,334 B1 * | 9/2001 | Moll et al. | 623/1.24 |
| 6,494,909 B2 * | 12/2002 | Greenhalgh | 623/1.24 |
| 7,785,364 B2 * | 8/2010 | Styrc | 623/1.24 |
| 7,967,853 B2 * | 6/2011 | Eidenschink et al. | 623/1.24 |
| 8,109,943 B2 * | 2/2012 | Boraiah et al. | 606/139 |
| 8,133,270 B2 * | 3/2012 | Kheradvar et al. | 623/2.11 |
| 2003/0187500 A1 * | 10/2003 | Jansen et al. | 623/1.26 |
| 2003/0209835 A1 * | 11/2003 | Chun et al. | 264/339 |
| 2004/0186558 A1 * | 9/2004 | Pavcnik et al. | 623/1.24 |
| 2004/0260389 A1 | 12/2004 | Case et al. | |
| 2005/0096736 A1 * | 5/2005 | Osse et al. | 623/1.26 |
| 2005/0137676 A1 * | 6/2005 | Richardson et al. | 623/1.11 |
| 2005/0143801 A1 | 6/2005 | Aboul-Hosn | |
| 2005/0182483 A1 * | 8/2005 | Osborne et al. | 623/1.24 |
| 2006/0178740 A1 * | 8/2006 | Stacchino et al. | 623/2.18 |
| 2006/0265053 A1 * | 11/2006 | Hunt | 623/1.24 |
| 2006/0276813 A1 * | 12/2006 | Greenberg | 606/158 |
| 2006/0282157 A1 * | 12/2006 | Hill et al. | 623/1.24 |

(Continued)

FOREIGN PATENT DOCUMENTS

| | | |
|---|---|---|
| WO | WO0154625 | 8/2001 |
| WO | WO0243620 | 6/2002 |

OTHER PUBLICATIONS

International Searching Authority, Written Opinion, Mar. 3, 2010, International application No. PCT/US2010/020331.

(Continued)

*Primary Examiner* — Thomas J Sweet  
*Assistant Examiner* — Seema Mathew  
(74) *Attorney, Agent, or Firm* — Buchanan Nipper

(57) ABSTRACT

An implantable valve prosthesis is provided. The valve prosthesis includes a frame structure having first and second independent frame elements. A graft member is attached to both the first and second frame elements and includes a closure member, such as a valve leaflet. The closure member is movable between a first position that allows fluid flow through the prosthesis in a first, antegrade direction and a second position that restricts flow through the prosthesis in a second, retrograde direction.

17 Claims, 10 Drawing Sheets

U.S. PATENT DOCUMENTS

| | | |
|---|---|---|
| 2007/0093887 A1* | 4/2007 | Case et al. .................... 623/1.24 |
| 2007/0239273 A1* | 10/2007 | Allen ........................... 623/2.38 |
| 2007/0244545 A1 | 10/2007 | Birdsall et al. |
| 2007/0288086 A1* | 12/2007 | Kalmann et al. ............. 623/1.24 |
| 2008/0183280 A1 | 7/2008 | Agnew et al. |
| 2009/0099653 A1* | 4/2009 | Suri et al. ..................... 623/2.11 |
| 2009/0105813 A1 | 4/2009 | Chambers et al. |
| 2009/0187241 A1* | 7/2009 | Melsheimer .................. 623/2.36 |
| 2009/0287296 A1* | 11/2009 | Manasse ...................... 623/1.18 |

OTHER PUBLICATIONS

PCT, International Search Report, Mar. 3, 2010, International application No. PCT/US2010/020331.

* cited by examiner

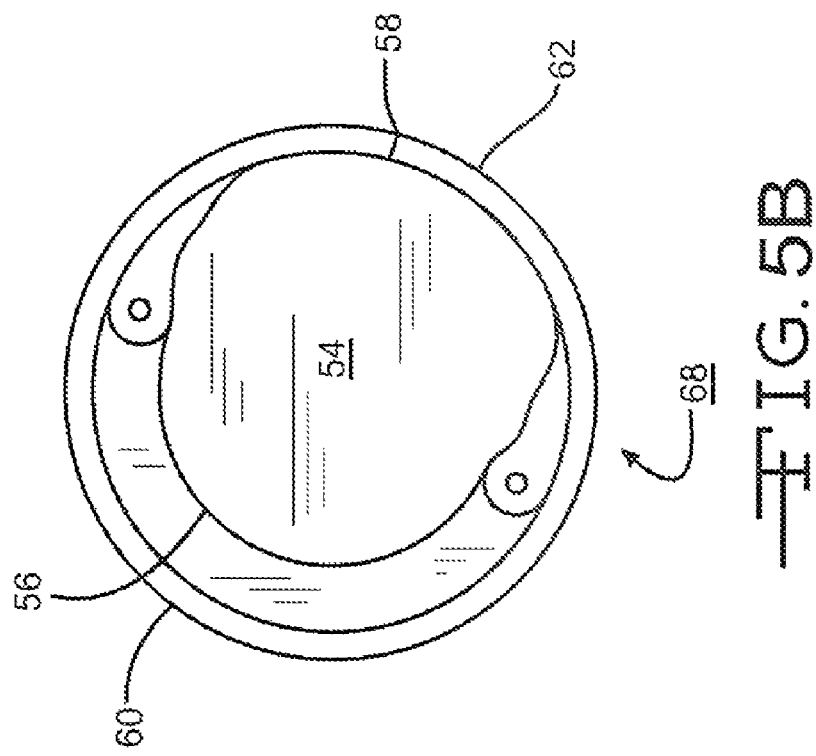
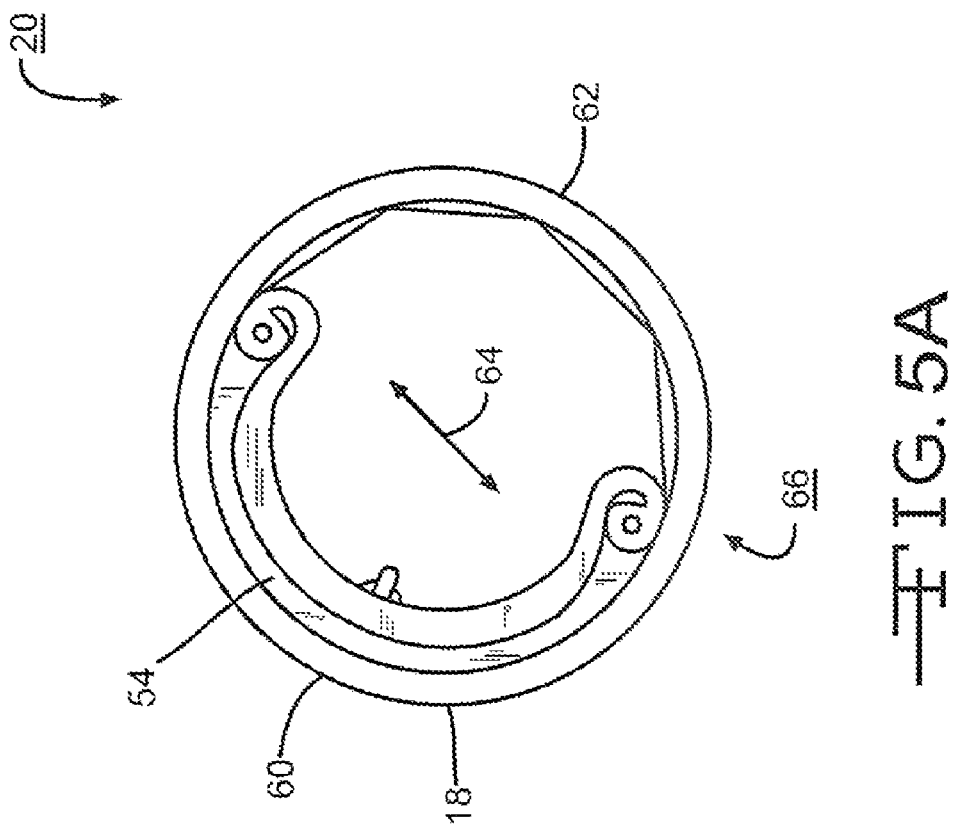
FIG. 5A
FIG. 5B

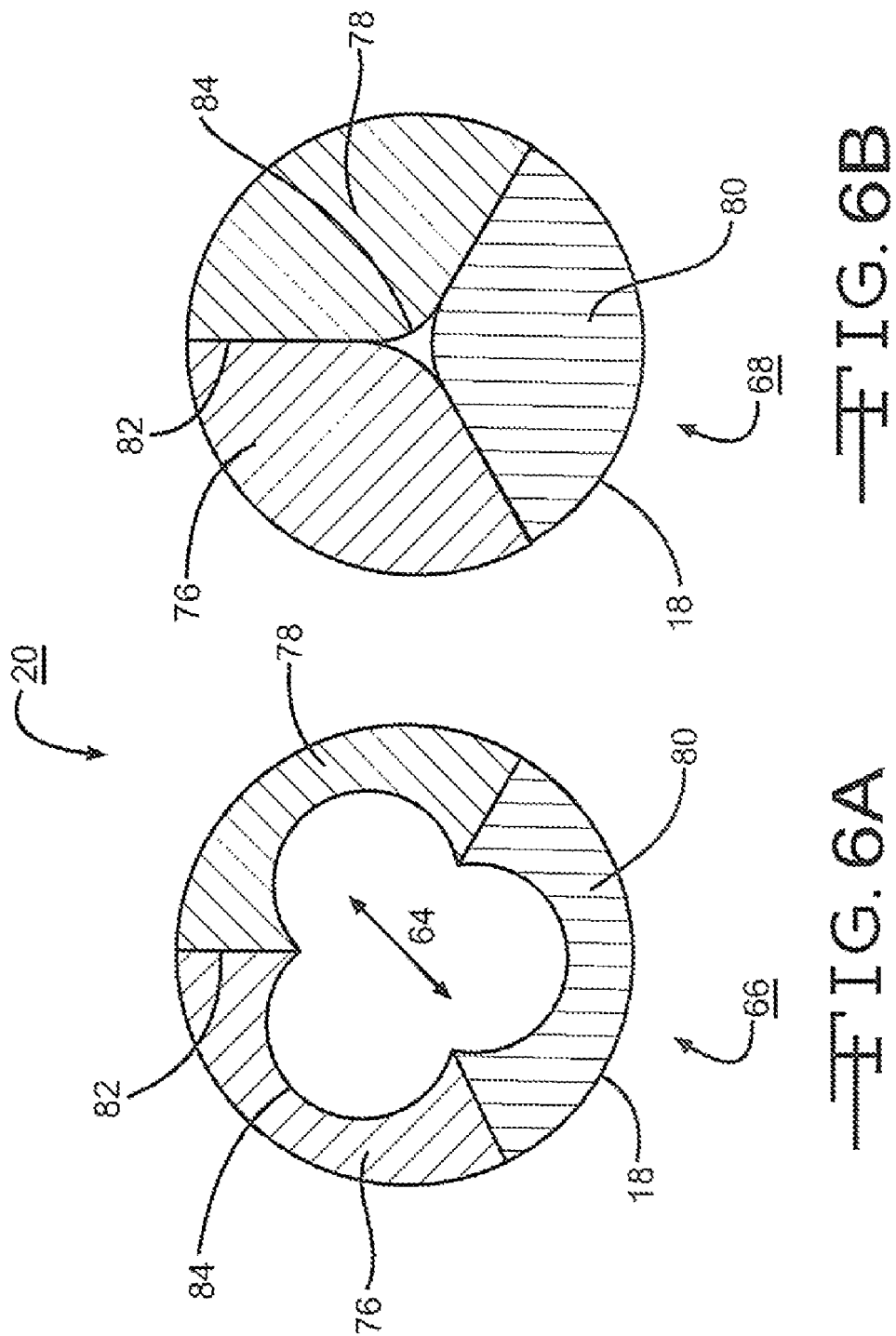

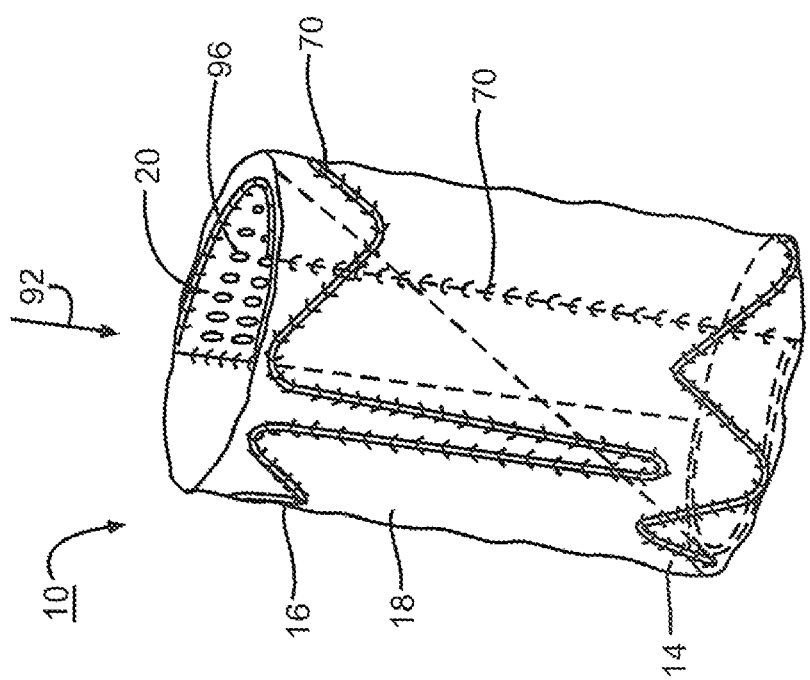
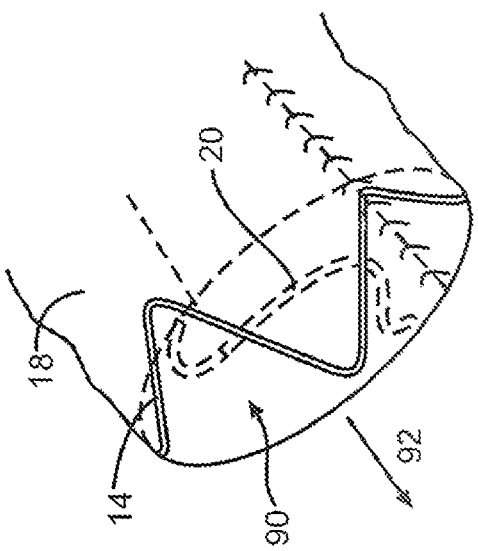

IMPLANTABLE VALVE PROSTHESIS WITH INDEPENDENT FRAME ELEMENTS

CROSS REFERENCE TO RELATED APPLICATION

This application claims priority to U.S. Provisional Application Ser. No. 61/142,940, filed on Jan. 7, 2009. The entire contents of this provisional application are hereby incorporated by reference into this disclosure.

FIELD

The disclosure relates to implantable medical devices. More particularly, the disclosure relates to implantable medical valve devices having support frames adapted for percutaneous implantation within a body vessel.

BACKGROUND

Many veins of the human body or animals include natural valves that aid in the return of blood flow toward the heart. These natural valves may prevent blood from pooling in the lower legs and feet. The proper function of these venous valves is especially important during standing or sitting when the weight of blood in the vein can slow blood flow toward the heart. Problems can arise when these venous valves fail to function properly. For example, venous valves can become incompetent or damaged by disease such that the backflow of blood is not prevented. When this occurs, blood pressure builds up and the veins and their valves become dilated, particularly in the lower extremities. If enough pressure builds up, the condition of venous insufficiency may develop. The severity of this condition is substantial, resulting in swelling, extensive pain, deformities, and, in the most severe cases, the development of ulcers can occur. If these ulcers become infected, amputation may ultimately be necessary to save the patient's life.

Currently, there is no proven cure for venous insufficiency. Basic treatments include elevation of the legs or the use of compression stockings. If surgery is determined to be necessary, vein stripping is typically performed, which involves the removal of the incompetent or damaged vein(s). Other surgical methods involve valvular reconstruction or transplantation.

The development of artificial and biological valves has been employed in an attempt to return normal pressure to the veins. There are a variety of these valves described in the art, which are generally designed to allow normal flow of blood back to the heart, while preventing retrograde flow. However, blood flow within a vein is intermittent and bidirectional, subject to constant fluctuation in pressure and volume. As a result, the shape of a lumen of a vein can undergo dramatic dynamic change resulting from these varying blood flow velocities, pressures and volumes therethrough. Many design considerations, consequently, regarding artificial valves for the venous system are taken into account. One primary consideration includes the ability of the frame and the valve to conform to the dynamic fluctuations in the shape of the lumen of the vein. Another primary consideration is the ability of the valve to be implanted in a body vessel having a variable diameter along the length of a site of implantation, or a branched body vessel site of implantation.

What is needed is an intraluminally-placed valve prosthesis, including a frame and valve, or closure member, that is compliant to be delivered percutaneously and, upon implantation, configured to prevent migration within the body vessel and minimize irritation of the body vessel. In addition, there remains a need for a valve prosthesis to conform to the changing shape of the lumen of the vein. There also remains a need for valve devices having a support frame configured with a radial strength to maintain patency of a body vessel while supporting a means for regulating fluid within the body vessel.

BRIEF SUMMARY OF THE DISCLOSURE

In one embodiment, an implantable valve prosthesis is provided to regulate fluid flow. The valve prosthesis comprises a frame structure and a graft member. The frame structure comprises a first frame and a second frame, wherein the first and second frames are independent. The graft member connects the first and second frames together. The graft member further comprises a closure member. The closure member is movable between a first position that allows flow in a first, antegrade direction and a second position that restricts flow in a second, retrograde direction.

In another embodiment, the valve prosthesis comprises a frame structure. The frame structure comprises a first frame and a second frame, wherein the first and second frames are independent. The frame structure further comprises the first frame having a proximal end and a distal end, and the second frame having a proximal end and a distal end. The frame structure further comprises the proximal end of the second frame being located at a distance closer to the proximal end of the first frame than a measured distance from the distal end of the first frame to the proximal end of the first frame, as measured along the longitudinal axis of the frame structure. The valve prosthesis further comprises a graft member which connects the first and second frames together. The graft member further comprises a closure member. The closure member is movable between a first position that allows flow in a first, antegrade direction and a second position that restricts flow in a second, retrograde direction.

In another embodiment, a method of manufacturing an implantable valve prosthesis comprises forming a first frame, wherein the first frame has a proximal end and a distal end. The method of manufacturing further comprises forming a second frame, wherein the second frame has a proximal end and a distal end. Additionally, the first and second frames are independent of each other, and the proximal end of the second frame is located at a distance closer to the proximal end of the first frame than a measured distance from the distal end of the first frame to the proximal end of the first frame, as measured along a longitudinal axis of the frame structure. The method of manufacturing further comprises attaching a graft member having a closure member to the first frame and the second frame. The closure member is movable between a first position that allows flow in a first, antegrade direction and a second position that restricts flow in a second, retrograde direction, thereby forming an implantable valve prosthesis.

BRIEF DESCRIPTION OF THE DRAWINGS

The following detailed description of specific embodiments of the present invention can be best understood when read in conjunction with the following drawings, where like structure is indicated with like reference numerals.

FIGS. 5a and 5b depict cross-sectional views of an embodiment of a monocusp leaflet valve, located within and connected to the graft member. FIG. 5a depicts a cross-sectional view of the monocusp valve in the open position, allowing antegrade flow. FIG. 5b depicts a cross-sectional view of the monocusp valve in the closed position, restricting retrograde flow.

FIGS. 6a and 6b depict cross-sectional views of an embodiment of a tricusp leaflet valve, located within and connected to the graft member. FIG. 6a depicts a cross-sectional view of the tricusp valve in the open position, allowing antegrade flow. FIG. 6b depicts a cross-sectional view of the tricusp valve in the closed position, restricting retrograde flow.

FIGS. 7a and 7b depict perspective views of an embodiment of an implantable valve prosthesis having a tubular valve closure member that controls fluid flow through movement between the lumen created by the frame structure. FIG. 7a depicts the embodiment the closure member in the closed position, restricting retrograde flow. FIG. 7b depicts a section of the closure member, wherein the closure member is in the open position, allowing antegrade flow.

DETAILED DESCRIPTION

Figure 1:
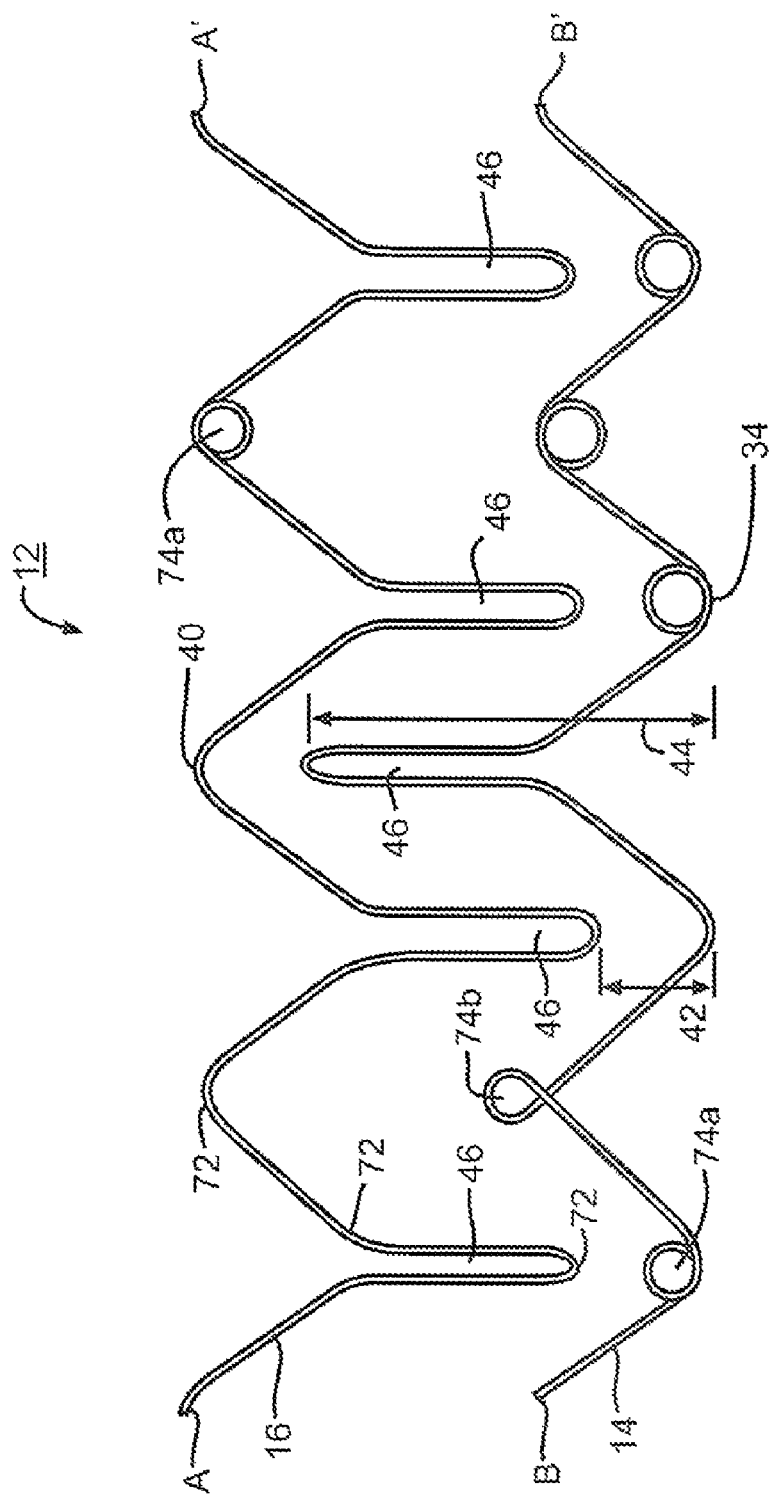
FIG. 1 is a flat plan view of an embodiment of the frame structure of an exemplary implantable valve prosthesis, wherein independent elements A-A' and B-B' can be circularized to form the three-dimensional frame structure.

For the purposes of promoting an understanding of the principles of the invention, reference will now be made to the embodiments illustrated in the drawings, and specific language will be used to describe the same.

In the following discussion, the terms "proximal" and "distal" are used to denote a direction or position relative to each other. Unless otherwise indicated, the recitation of "proximal" or "distal" portions of a frame does not refer to any particular orientation of the implantable valve prosthesis within a body. The implantable valve prosthesis described herein can be used in many different body lumens, including both the arterial and venous system, and can be implanted in any suitable orientation within the body. Specifically, in terms of venous blood flow, the term "proximal" may refer to the direction of antegrade venous blood flow toward the heart, while "distal" may refer to a direction of retrograde venous blood flow away from the heart.

As used herein, the term "circumferential" or "circumferentially" refers to a direction or displacement measured along the exterior surface area of an implantable frame that is transverse to the longitudinal axis of the implantable frame.

As used herein, the term "longitudinal" or "longitudinally," unless otherwise indicated, refers to a direction measured along the longitudinal axis of the medical device, or a portion thereof such as an implantable frame.

As used herein, terms such as "preferably," "desirably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used herein, the term "longitudinal strut" may refer to a formation along either the first or second frame in which a section of the frame is positioned to run from a starting point that is at approximately one end of the implantable frame along a substantial portion of the longitudinal axis of the implantable frame, and then end by returning to the same end of the implantable frame, at a location a short distance from the starting point. Typically, a substantial portion of the longitudinal axis refers to at least 50% of the length measured from the distal end of the second frame to the proximal end of the first frame.

As used herein, the term "graft member" may refer to a flexible material used to connect the frame structure together. Examples of suitable natural materials include collagen and extracellular matrix (ECM) materials, such as small intestine submucosa (SIS), and other bioremodelable materials, such as bovine pericardium. Other non-limiting examples of ECM materials that can be used for the graft member include stomach submucosa, uterine submucosa, urinary bladder submucosa, tissue mucosa, basement membrane materials (such as liver basement membrane), renal capsule, serosa, peritoneum, dura matter, pericardium or other tissues. Examples of suitable synthetic materials include polymeric materials, such as expanded polytetrafluoroethylene and polyurethane, among others.

As used herein, the term "closure member" may refer to the valve located within the frame structure and graft member. The closure member is movable between a first position that allows flow in a first, antegrade direction and a second position that restricts flow in a second, retrograde direction. Typically, the closure member refers to a leaflet-type valve structure or a tubular or other non-leaflet type valve structure. The closure member may be made from a similar, flexible material as the graft member.

Implantable, intraluminally-placed valve prostheses provided herein are configured to be negotiated through tortuosity more easily during introduction into the body vessel. The implantable valve prosthesis include one or more of the structural features described in the various embodiments herein. These structural features relate generally to the configuration of implantable valve prostheses that include independent frame elements connected by a graft member.

The implantable valve prosthesis is designed to be percutaneously delivered through a body lumen to a target site in the venous system adjacent to an insufficient venous valve. An appropriately sized delivery catheter can be selected by one of skill in the art for the given application. For example, some embodiments may use a delivery catheter selected from one or more delivery catheter sizes from the group consisting of 1-30 french (F) delivery catheters, or increments of 0.1 F therebetween. In some embodiments, a delivery catheter sized between 1 and 25 F can be used. In other embodiments, the delivery catheter can be sized between 1.5 and 5 F can be used. The inventors have determined that a delivery catheter sized between 8 and 21 F is particularly advantageous for use with implantable valve prosthesis as described herein. For venous valve embodiments in which the graft member comprises a fixed tissue valve, as described below, the inventors have determined that a delivery catheter sized between 13 and 17 F is particularly advantageous at least because it is sufficiently large in size to accommodate the bulk of the valve prosthesis yet sufficiently small in size to allow the catheter to navigate and deliver the prosthesis to intended points of treatment in the vasculature.

In certain embodiments, the implantable valve prosthesis is delivered to the desired site in a compacted form. Upon reaching the site, the valve prosthesis can be expanded and securably placed within the body vessel, for example by securably engaging the walls of the body vessel lumen. The expansion mechanism may involve forcing the valve prosthesis to expand radially outward, for example, by inflation of a balloon formed in the distal portion of the catheter, to inelastically deform the valve prosthesis and fix it at a predetermined expanded position in contact with the lumen wall. The expansion balloon can then be deflated and the catheter removed. In another embodiment, the frame of the implantable valve prosthesis is formed of an elastic material that will self-expand by its own internal elastic restoring force upon removal of a constraining force, such as a force placed on the frame by a surrounding sheath of a delivery catheter in which an implantable valve prosthesis that includes the frame is disposed.

Figure 2:
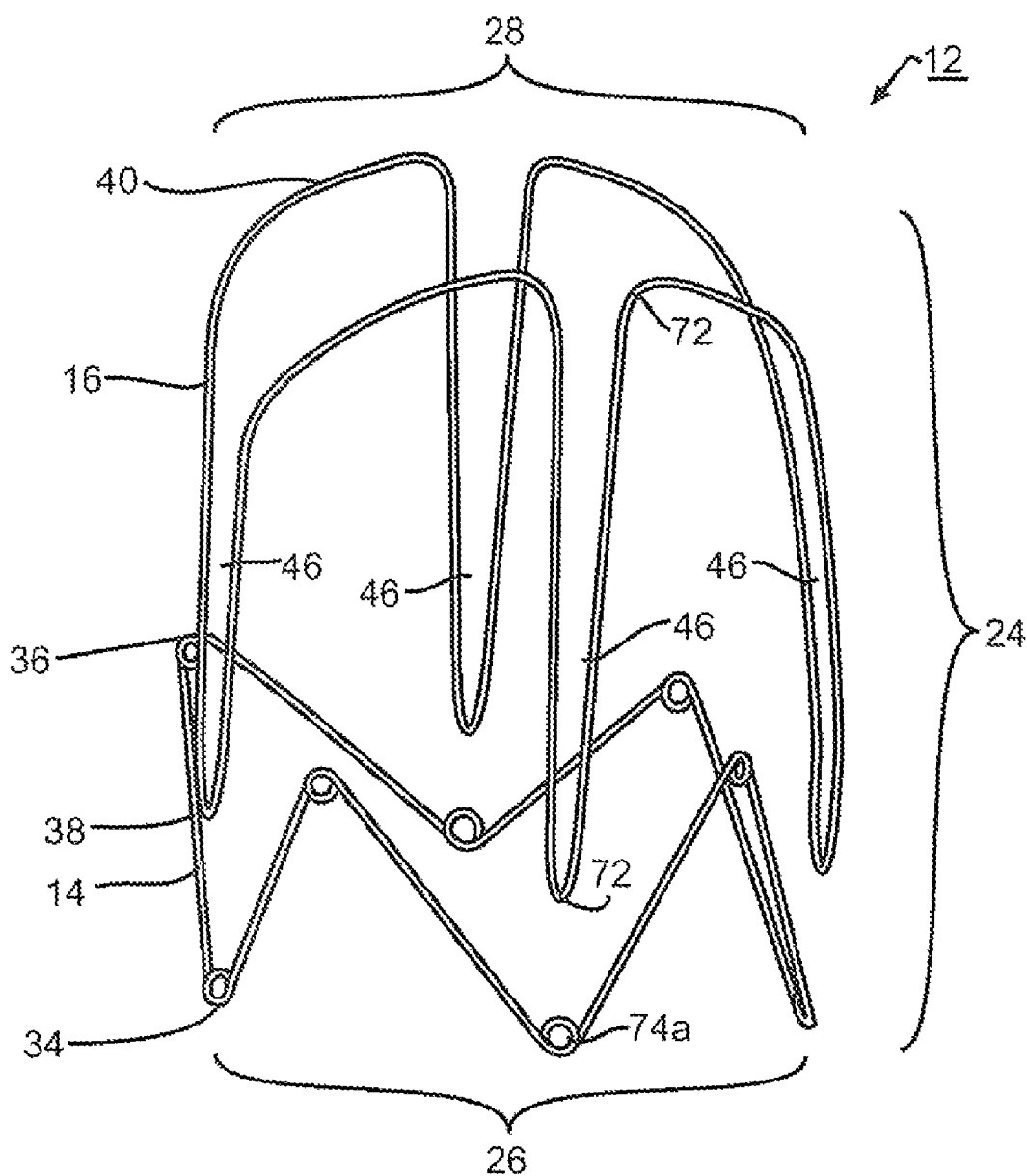
FIG. 2 depicts a perspective view of an embodiment of a frame structure having a first frame and second frame.

As shown in the embodiments of FIGS. 1 and 2, the implantable, intraluminally-placed valve prosthesis contains a frame structure 12 having a first frame 14 and a second frame 16. The first frame 14 and second frame 16 are independent of each other. The inclusion of two independent frame elements is considered advantageous at least because it is expected to provide additional flexibility to the implantable valve prosthesis and relieve stress that might otherwise be placed on a unitary frame structure during navigation through a body vessel or simply by the nature and/or configuration of such a unitary frame. Furthermore, the use of two independent frame elements facilitates the manufacturing of complex frame configurations and/or geometries and structures, particularly when spring metals that provide plastic deformation are used (e.g., stainless steel).

Figure 3:
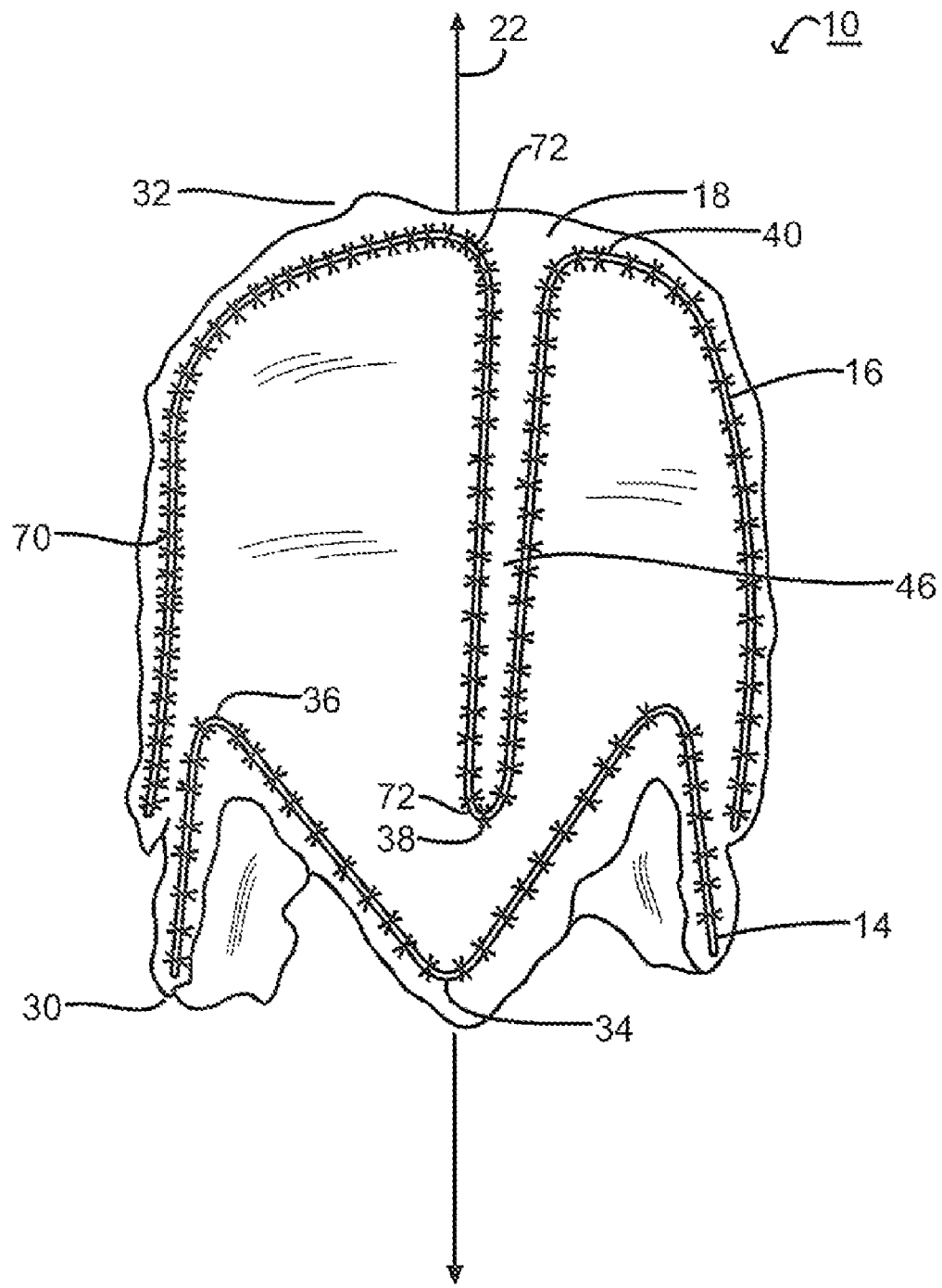
FIG. 3 depicts a schematic view of an embodiment of the implantable valve prosthesis, wherein graft material is connected to the frame structure. In this embodiment, the connection is made via stitches or sutures.

As shown in FIG. 3, the first frame 14 and second frame 16 are separated by various gaps as measured along the longitudinal axis 22. The first frame 14 and second frame 16 are connected by a graft member 18 having a closure member. The connection between frames 14, 16 by the graft member 18 is the only connection between the frames 14, 16. The frames 14, 16 do not connect directly with or otherwise contact each other while the valve prosthesis 10 is in a resting state. The frame structure 12 and graft member 18 thereby form the intraluminally-placed valve prosthesis 10. While many of the illustrative embodiments provide implantable valve prostheses 10 having a first frame 14 and a second frame 16, other embodiments comprising three or more frame elements are also possible. These additional frame elements may be longitudinally aligned with the first frame 14 and second frame 16 by being centered on a common longitudinal axis 22 when the valve prosthesis 10 is in an expanded configuration within the body vessel. In embodiments with three or more frame elements, at least two of the frame elements are independent from each other, wherein the frame elements are not in direct contact with each other, but are instead separated by a gap. In other embodiments, every frame element is independent from all other frame elements.

Using a graft member, such as a tissue valve or other section of tissue, as described below, to connect the independent frames 14, 16 confers structural stability onto the valve prosthesis without sacrificing the flexibility provided by the independent frames 14, 16.

Additionally, it is noted that the orientation of the frame elements, such as the first frame 14 and second frame 16, may be in either direction along the longitudinal axis 22 within the body vessel.

As shown in FIG. 2, the frame structure 12 can have any size (i.e. length, diameter) suitable for intralumenal implantation. The longitudinal length 24 of the frame structure 12, as measured along the longitudinal axis, may be greater than 50 mm. In certain embodiments, the longitudinal length 24 is between approximately 5 mm and 50 mm, and any increment of approximately 0.10 mm or 0.25 mm thereof.

Having a frame structure 12 with a first frame 14 that is independent from the second frame 16 allows for a variety of configurations. In certain embodiments, such as the embodiment shown in FIG. 2, the frame structure 12 can accommodate varying sizes of first frame expanded diameters 26 and second frame expanded diameters 28 due to the independence of the frame structure elements. As used herein, "expanded diameter" may be defined as the measured diameter of the frame structure element after it has been deployed within the vessel and expanded to contact the vessel wall. The expanded diameters of the first and second frames in the expanded configuration can be selected by one skilled in the art given the desired location for implantation. When in a compressed state for delivery to a desired location within a body lumen, the implantable valve prosthesis 10 is typically reduced from about two to about six times the diameter of the prosthesis when it is in an expanded state. Some frame elements may have a compressed external diameter of about 1-5 mm or more and an expanded external diameter of up to about 25 mm, including between about 1 and 25 mm.

Furthermore, the frames 14, 16 can have the same or different expansion diameters. For example, one frame member that is positioned at a proximal end of the valve prosthesis can have a greater expansion diameter than the frame member that is positioned at the distal or opposite end of the valve prosthesis. The use of differing expansion diameters can provide one end with enhanced anchoring characteristics, which may be desirable in valve prosthesis that include tissue graft members or graft members formed of bioremodellable materials where sealing contact with a vessel wall is considered advantageous. In these embodiments, either frame member, located at either end of the valve prosthesis, can have the greater expansion diameter and a skilled artisan can determine a desirable configuration for a particular valve prosthesis based on various considerations, including the nature and orientation of the graft member.

Due to the independence of the frame elements, the expanded diameters may differ from each other. For example, it is possible for the first frame expanded diameter 26 to be approximately 10% greater than the second frame expanded diameter 28. It is also possible for the first frame expanded diameter 26 to be 20%, 30%, 40%, 50%, 60%, 70%, 80%, 90%, 100%, or >100% greater than the second frame expanded diameter 28. In other embodiments, it is possible for the first frame expanded diameter 26 to be 10% less than the second frame expanded diameter 28. It is also possible for the first frame expanded diameter 26 to be 20%, 30%, 40%, 50%, 60%, 70%, 80%, 90%, 100%, or >100% less than the second frame expanded diameter 28.

Various materials may be used in construction of the frame structure 12. In certain embodiments, the materials for the frame elements include those materials that can provide the desired functional characteristics with respect to mechanical load bearing, biological compatibility, modulus of elasticity, radio-opacity, corrosion resistance, or other desired properties. For certain embodiments, the frame elements can comprise a metal, a metal alloy, a polymer, or any suitable combination thereof, such as a frame with multiple layers.

Certain embodiments comprise frame elements made from material with a low yield stress (to make the frame deformable at manageable balloon pressures), high elastic modulus (for minimal recoil), and work-hardened through expansion for high strength.

In certain embodiments, the frame materials for self-expanding implantable valve prostheses include shape memory alloys that exhibit superelastic behavior, i.e., materials that are capable of significant distortion without plastic deformation. Frames manufactured of such materials may be significantly compressed without permanent plastic deformation, i.e., they are compressed such that the maximum strain level in the valve prosthesis is below the recoverable strain limit of the material. Nickel titanium alloys and other alloys that exhibit behaviors suitable for the frame elements are discussed in U.S. Pat. No. 5,597,378 (Jervis) and WO 95/31945 (Burmeister et. al.), herein incorporated by reference. In one embodiment, the shape memory alloy for the frame structure is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, Cu—Zn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired, as is known in the art. Ni—Ti alloys suitable for use in manufacturing the frame elements of an implantable valve prosthesis can be obtained from, e.g., Memory Corp., Brookfield, Conn. One suitable material possessing desirable characteristics for self-expansion is NITINOL®, a nickel-titanium alloy that can recover elastic deformations of up to 10%. This unusually large elastic range is commonly known as superelasticity. Tertiary nickel-titanium alloys, which include nickel, titanium and another metal, are also considered suitable and are believed to provide particular advantages, including beneficial strength and flexibility characteristics. Ni—Ti—Cr is one example of a suitable tertiary nickel-titanium alloy.

In certain embodiments, the implantable frames are manufactured from an inert, biocompatible material with high corrosion resistance that can be plastically deformed at low-moderate stress levels, such as tantalum. The implantable frames can be deployed by both assisted/mechanical expansion (e.g., balloon expansion), and self-expansion means. In embodiments where the implantable frame is deployed by mechanical expansion, the implantable frame is made from materials that can be plastically deformed through the expansion of a mechanical assist device (e.g., a catheter based balloon). When the balloon is deflated, the frame can remain substantially in the expanded shape. In addition to tantalum, other acceptable materials include stainless steel, titanium ASTM F63-83 grade 1, niobium or high carat gold K 19-22. One widely used material for balloon expandable frame structures is stainless steel, particularly 316L stainless steel which has corrosion resistant properties, a low carbon content and the additions of molybdenum and niobium. Alternative materials for mechanically expandable structural frames that maintain similar characteristics to stainless steel include tantalum, platinum alloys, niobium alloys, and cobalt alloys.

In certain embodiments, the frame elements may be formed from or coated with other materials, such as polymers and bioadsorbable polymers. For example, the frames can comprise (that is, be formed from or coated with): polyethylene (PE); polypropylene (PP); polyisobutylene; poly(alpha olefin); alkyl (alkyl)acrylates such as poly(n-butyl methyacrylate) (PBMA), poly(methyl acrylate) or poly(methyl methacrylate) (PMMA); parylenes such as parylene C; ethyl vinyl acetate (EVA); poly(ethylene-co-vinyl acetate) (PEVA), or copolymers or mixtures thereof.

In other embodiments, it may be desirable to provide frame elements comprising bioabsorbable polymers including polyesters such as poly(hydroxyalkanoates), poly(lactic acid) or polyactide (PLA), poly(glycolic acid) or polyglycolide (PGA), poly(caprolactone), poly(valerolactone) and co-polymers thereof; polycarbonates; polyoxaesters such as poly (ethylene oxalate), poly(alkylene oxalates); polyanhydrides; poly(amino acids); polyphosphazenes; phosphorylcholine; phosphatidylcholine; various hydrogels; polydioxanone, poly(DTE carbonate) and co-polymers or mixtures of two or more polymers. The frame elements can also include various natural polymers such as fibrin, collagens, extracellular matrix (ECM) materials, dextrans, polysaccharides, and hyaluronic acid.

Additionally, in certain embodiments, the frame structure 12 can comprise certain materials that permit identification of the position or orientation of the frame structure within a body passage. Radiopaque markers are advantageously positioned at one or more ends of the frame structure to aid the physician in positioning the frame structure at a site inside a body vessel. For example, portions of the frame structure can include a radiopaque material that can be identified by X-ray. The frame structure may also comprise materials that are useful with contrast dyes to identify the frame within a body vessel. Numerous radiopaque materials are known in the art, such as those described in U.S. Pat. No. 6,409,752 (Boatman et al.), herein incorporated by reference. Examples of radiopaque materials include, but are not limited to, high-density metals such as platinum, iridium, gold, silver, tantalum or their alloys, or radiopaque polymeric compounds. Radiopaque materials may be highly visible under fluoroscopic illumination and may be visible even at minimal thickness.

Regarding methods of manufacture of the frame elements, the frame elements may be fabricated using any suitable method known in the art. Such nonlimiting examples such as laser-cutting, water-jet cutting, and photochemical etching are all methods that can be employed to form the structural frame from sheet or tube stock. In certain embodiments, the frame elements can be formed from wire using wire forming techniques, such as coiling, braiding, or knitting. The method of fabrication can be selected by one skilled in the art depending on the raw material used. Forming the frame elements from wires of spring metals that give plastic deformation, such as stainless steel, using wire forming techniques is considered advantageous at least because it allows for the formation of coils or other bends in the frame elements. The inclusion of such complex geometries and configurations, while considered optional, may be beneficial because they can enhance the overall flexibility of the frame elements and provide desirable radial force characteristics to the frame. Furthermore, the inclusion of coils and/and bends is beneficial to the fatigue life of the frame structure.

The frame structure 12 can optionally be sterilized using any suitable technique known in the art, or equivalents thereto. For example, a frame structure can be sterilized using ethylene oxide sterilization, as described in AAM/ISO 11135:1994 "Medical Devices—Validation and Routine Control of Ethylene Oxide Sterilization," herein incorporated by reference.

In one embodiment, as shown in FIG. 1, the frame structure comprises undulating frame elements. The undulating frames are typically formed with a number of struts and/or bends that are joined to form a closed hoop structure. Each bend can have a similar or a different configuration from the other bends. The configurations may be arcuate or "V"-shaped configurations 72. Additionally, in one embodiment, at least one bend in the frame structure comprises a "safety-pin" spring-section element 74a or 74b. The safety-pin element 74a or 74b may be located on any number of the frame elements, including the first frame or the second frame, or both frame elements. As seen in FIG. 1, several safety pin spring section elements 74a and 74b are present in which the frame-wire loops around itself to form a coil, creating a spring element and adding to the flexibility and longevity of the frame structure. The safety-pin elements 74a and 74b may be constructed in a number of ways, including, but not limited to, the constructions shown in FIG. 1. Typically, safety-pin elements 74a and 74b may be used with a wire frame made from steel or similar material. Also, typically, arcuate configurations 72 are present in shape-memory frames such as Ni—Ti alloys.

Figure 4:
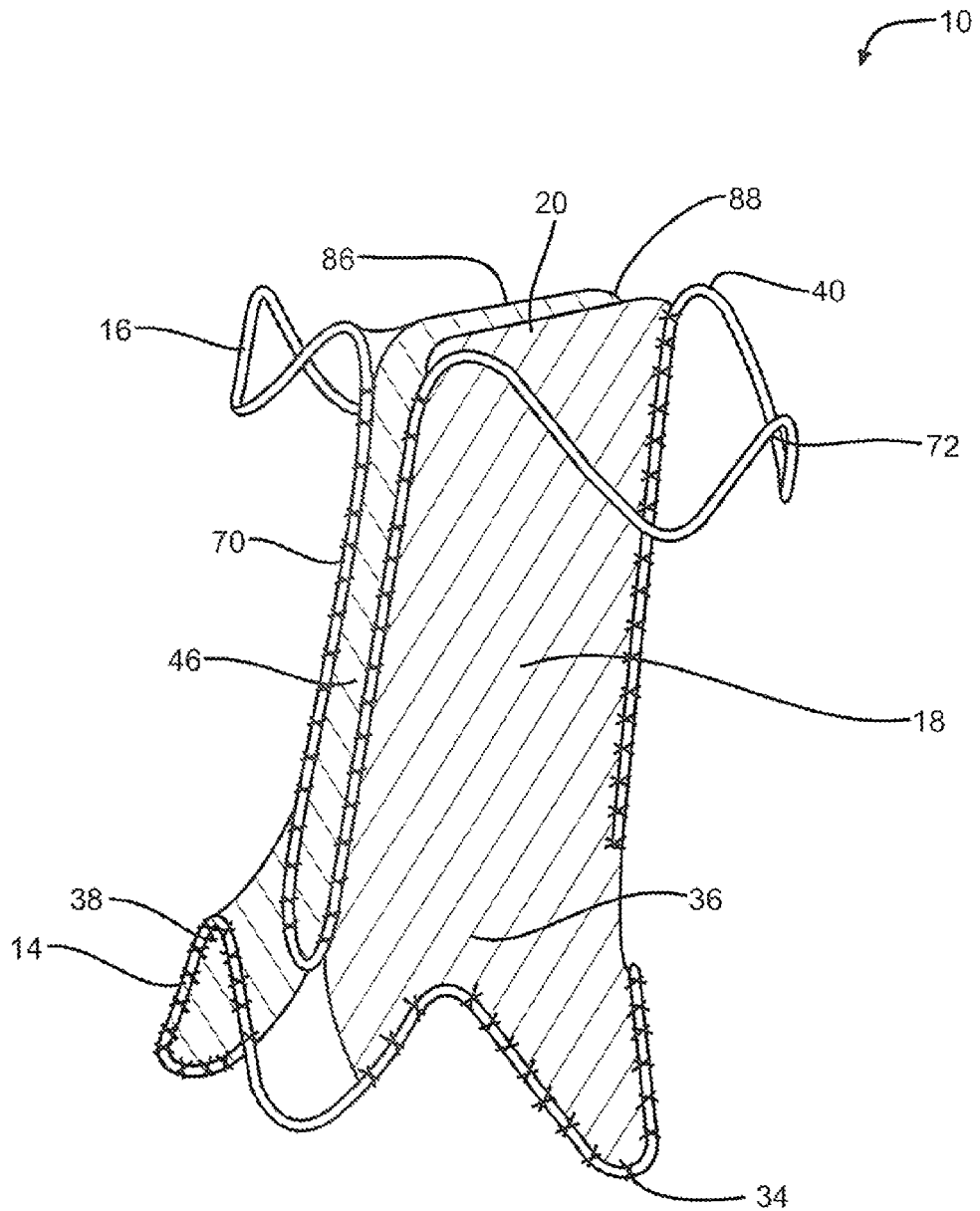
FIG. 4 depicts a perspective view of an embodiment of an implantable valve prosthesis having a bicusp valve closure member connecting the first and second frame elements.

FIG. 2 depicts other embodiments of arcuate configurations 72 and safety-pin element configurations 74a forming the frame elements. FIGS. 3 and 4 also depict embodiments of the arcuate configurations 72 as well.

Also regarding the frame structure 12, in certain embodiments, the first frame 14 and second frame 16 "overlap" each other. Overlapping can be defined in terms of the frame structure elements. As shown in FIG. 1, the frame structure 12 has a first frame 14 and a second frame 16. The first frame 14 has a proximal end 34 and a distal end 36, and the second frame 16 has a proximal end 38 and a distal end 40. The overlapping may involve having the proximal end 38 of the second frame 16 located at a shorter distance 42 to the proximal end 34 of the first frame 14 than the measured distance 44 between the distal end 36 of the first frame 14 and the proximal end 34 of the first frame 14, as measured along the longitudinal axis of the frame structure 12.

The overlapping may be achieved through bends and struts present on the frame elements. In certain embodiments, the frame structure contains at least one longitudinal strut 46. The longitudinal struts 46 may be located on any or all frames, including the first frame 14 and second frame 16. The longitudinal struts 46 assist in having the frame structure elements overlap each other. For example, in FIGS. 1 and 2, four longitudinal struts 46 are present on the second frame 16 that overlaps with the first frame 14. Additionally, as shown in FIG. 1, one longitudinal strut 46 is present on the first frame 14 that overlaps with the second frame. In the embodiment shown in FIG. 1, the proximal end 38 of the longitudinal strut 46 on the second frame 16 is located at a shorter distance 42 to the proximal end 34 of the first frame 14 than the measured distance 44 between the distal end 36 of the first frame 14 and the proximal end 34 of the first frame 14.

The independent frame structure elements (such as the first frame 14 and second frame 16) are connected to each other via a graft member 18, as shown in FIG. 3. In certain embodiments, the graft member 18 and closure member are formed of a flexible material. Examples of suitable flexible materials for the graft member 18 and closure member include natural materials, synthetic materials, and combinations of natural and synthetic materials.

Examples of suitable synthetic materials include polymeric materials, such as polyesters like poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

In addition, the material of the graft member 18 or closure member 20 may be a biocompatible polyurethane or derivative thereof. One example of a biocompatible polyurethane is THORALON (THORATEC, Pleasanton, Calif.), as described in U.S. Provisional Application No. 61/022,750, U.S. Patent Application Publication No. 2002/0065552, and U.S. Pat. No. 4,675,361, the entire contents of each of which are hereby incorporated into this disclosure by reference.

Examples of suitable natural materials include collagen and extracellular matrix (ECM) materials, such as small intestine submucosa (SIS), and other bioremodelable materials, such as bovine pericardium. The "extracellular matrix" is typically a collagen-rich substance that is found between cells in animal tissue and serves as a structural element in tissues. Other non-limiting examples of ECM materials that can be used for the graft member 18 include stomach submucosa, uterine submucosa, urinary bladder submucosa, tissue mucosa, basement membrane materials (such as liver basement membrane), renal capsule, serosa, peritoneum, dura matter, pericardium or other tissues.

For additional information as to submucosa materials, and their isolation and treatment, reference can be made to U.S. Pat. Nos. 4,902,508; 5,554,389; 5,993,844; 6,099,567; and 6,206,931, the entire contents of each of which are hereby incorporated into this disclosure by reference. Renal capsule tissue can also be obtained from warm blooded vertebrates, as described more particularly in U.S. patent application Ser. No. 10/186,150, filed Jun. 28, 2002, and International Patent Application Serial Number PCT/US02/20499, filed Jun. 28, 2002, and published Jan. 9, 2003 as International Publication Number WO 03002165, the entire contents of each of which are hereby incorporated into this disclosure by reference. In one embodiment of the invention, the ECM material is porcine SIS. SIS can be prepared according to the method disclosed in U.S. 2004/0180042A1, the contents of which are incorporated herein by reference. In addition to xenogenic biomaterials, such as SIS, autologous tissue can be harvested as well. Additionally Elastin or Elastin Like Polypeptides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

The graft member can also comprise at least one leaflet and a contiguous wall portion harvested from a natural valve, such as a multi-leaflet vascular valve harvested from a xenogeneic source. Examples of such graft members are described in United States Patent Application Publication No. 20090105813 to Chambers et al. for IMPLANTABLE VALVE DEVICE, the entire contents of which are hereby incorporated into this disclosure by reference. The use of a fixed natural tissue valve, such as a single leaflet having a contiguous wall portion that has been harvested from a multi-leaflet natural valve, is considered particularly advantageous.

The inventors have determined that the use of independent frame elements in a valve prosthesis containing a fixed tissue valve, such as the monocusp tissue valve described above, is particularly advantageous at least because it facilitates manufacturing of a complex frame geometry that provides desirable attachment pathways along which the tissue valve can be connected to the frame elements. Furthermore, the inclusion of independent frame elements reduces the bulk of the frame and, as a result, the bulk of the overall valve prosthesis. This can be important in these valve prostheses because such fixed tissue valves can contribute significant bulk to the overall device. Reducing bulk provided by the frame lessens the concern about bulk contributed by the fixed tissue valve.

The inclusion of independent frame elements in a valve prosthesis is also considered advantageous because it improves the fatigue resistance of the frame structure when the prosthesis is implanted in a location that exerts a stress on the frame, such as elongation or torsional loading. With multiple independent frame elements, the frame structure is not inhibited from bending or elongating in response to such stress, allowing the frame to respond by bending, twisting, or elongating as appropriate. For example, a venous valve prosthesis implanted in the popliteal vein is subject to a torsional load as a result of its proximity to the knee. A prosthesis that includes multiple independent frame elements can respond to this load by twisting and/or rotating as appropriate, while a prosthesis that includes a single unitary frame structure would be force to bend at one or more struts or other structural features of the frame structure.

ECM materials are particularly well-suited materials for use as the graft member 18, at least because of their abilities to remodel and become incorporated into adjacent tissues. These materials can provide a scaffold onto which cellular in-growth can occur, eventually allowing the material to remodel into a structure of host cells. The connection between the graft member 18 and frame structure 12 helps define a flexible, non-stiff implantable valve prosthesis that may be negotiated through tortuosity more easily during introduction into the body vessel.

The graft member 18 may be formed by joining multiple sheets of biological material together. The sheets of biological material may be hydrated or dehydrated. Optionally, an adhesive, glue or other bonding agent may be used in achieving a bond between ECM layers within the graft member 18. Drying or dehydration methods can also be used to fuse ECM portions of the graft member 18. In one embodiment, the multiple layers of ECM material are compressed under dehydrating conditions. The term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions. Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

The thickness of the graft member 18 may be selected to provide a desired flexibility for a particular application. One way to alter the thickness of a graft member 18, such as a sheet formed from SIS material, is to compress it under dehydrating conditions, e.g., to vacuum press it. Another way to after the thickness of a multi-laminate graft member material formed from SIS material is to after the number of material layers included therein. A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used.

The graft member 18 may be connected to the frame structure elements in any suitable manner. In one embodiment, the graft member 18 may be stitched or sutured to the first frame 14 and second frame 16. As seen in FIG. 3, the graft member 18 is secured to the frame structure with stitches or sutures 70. Alternatively, adhesives, heat sealing, tissue welding, weaving, cross-linking, or any other suitable means may be used for attaching the graft member 18 to the frame structure elements. The means of connecting may depend at least upon the materials used for the graft member 18 and frame structure 12. Furthermore, the frame elements can be attached to an external surface of the graft member, as illustrated, or can be attached to an internal surface. Furthermore, one frame element can be attached to an external surface of the graft member while the other frame element can be attached to the internal surface. Furthermore, one or more portions of one or both frame elements can be attached to an external surface of the graft member while one or more other portions of one or both frame elements are attached to an internal surface of the graft member.

As previously noted, the implantable valve prosthesis 10 comprises a graft member 18, wherein the graft member 18 has a closure member 20. Various embodiments of closure members are shown in FIGS. 4-6. FIG. 4 represents one embodiment having a bicusp valve closure member. FIGS. 5a and 5b represent an embodiment having a monocusp valve closure member. FIGS. 6a and 6b represent an embodiment having a tricusp valve closure member. The closure member 20 is movable between a first position that allows flow in a first, antegrade direction and a second position that restricts flow in a second, retrograde direction. The closure member 20 may be made from a similar type of flexible material as the graft member, discussed above. In certain embodiments, the closure member 20 and graft member 18 are made from the same type of flexible material. In other embodiments, the closure member 20 and graft member 18 are made from different combinations of flexible material.

In certain embodiments, the closure member 20 is connected to the internal wall of the graft member 18. It is possible for the closure member 20 to be connected to the internal wall of the graft member 18 at a variety of locations along the implantable valve prosthesis 10. For example, in one embodiment, the closure member 20 is connected to the internal wall of the graft member 18 along the first frame 14.

In another embodiment, the connections are made to the internal wall of the graft member 18 along the second frame 16. In another embodiment, the connections are made to the internal wall of the graft member 18 at specified locations situated between the proximal end 30 and distal end 32 of the frame structure 12.

In one embodiment, shown in FIG. 4, the closure member 20 is connected to both the first frame 14 and the second frame 16. In this particular embodiment, the closure member 20 of the graft member 18 functions as the connection mechanism between the independent frame elements. In the embodiment shown in FIG. 4, the graft member 18 is different in the amount of material contacting the frame elements in comparison to the embodiment shown in FIG. 3 that has a substantial amount of the frame structure in contact with the graft member material.

The closure member 20 may be securably attached to the graft member 18 by any suitable means, including but not limited to, adhesives, fasteners, tissue welding using heat and/or pressure, binders, chemical bonding, vapor deposition, spraying, electrostatic deposition, ultrasonic deposition, dipping, and/or attachment by mechanical means, such as welding, suturing, sewing, threading, bonding, clamping, or otherwise affixed onto the graft member 18. Suitable bonding agents may include, for example, collagen gels or pastes, gelatin, or other agents including reactive monomers or polymers, for example cyanoacrylate adhesives. Also, bonding can be achieved or facilitated using chemical cross-linking agents, such as glutaraldehyde, formaldehyde, epoxides, genipin or derivatives thereof, carbodiimide compounds, polyepoxide compounds, or other similar agents. Cross-linking of ECM materials can also be catalyzed by exposing the ECM to UV radiation, by treating the collagen-based matrix with enzymes such as transglutaminase and lysyl oxidase, and by photocross-linking. The combination of one or more of these with dehydration-induced bonding may also be used.

In certain embodiments, the closure member 20 is a leaflet-type valve structure. In certain embodiments, a single leaflet-type valve or monocusp valve 54 is used. Monocusp valves are described in U.S. Provisional Application for Patent No. 61/022,750, the entire contents of which are hereby incorporated by reference. A non-limiting example of a suitable monocusp valve 54 is shown in FIGS. 5a, 5b. The single leaflet 54 can be attached to the graft member 18 and positioned within the opening of the frame structure. In one embodiment, the single leaflet 54 has a first edge 56 and a second edge 58. The first edge 56 can be disposed or attached to the graft member 18, while the second edge 58 can extend between a first side 60 and a second side 62, opposite the first side 60, of the graft member 18. The second edge 58 can be movable across the fluid flow path 64. Since the second edge 58 can be moveable, the second edge 58 can have an open position 66, as shown in FIG. 5a. The second edge 58 can have a closed, or substantially closed, position 68 to regulate fluid flow through fluid flow path 64, as shown in FIGS. 5a, 5b.

The single leaflet 54 can be oriented with the open end of the cone shape facing the direction of longitudinal retrograde fluid flow through fluid flow path 64. Referring to FIGS. 5a, 5b, during retrograde fluid flow, fluid (e.g., blood) passes the second edge 58 along the first side 60 of the single leaflet 54, urging the second edge 58 to transversely cross the fluid flow path 64 and sealably engage the wall of the body vessel as fluid fills the interior (i.e. "cup") portion of single leaflet 54. The single leaflet 54 quickly fills with the retrograde flowing fluid, preventing retrograde fluid flow from flowing through the implantable valve prosthesis and causing the single leaflet 54 to assume the closed position 68. In the closed position 68, fluid fills the interior cone or pocket of the single leaflet 54, which completely fills the fluid flow path 64 and prevents retrograde fluid flow through the valve device.

In certain embodiments, the closure member 20 may include "holes" or small openings in the closure member 20, allowing a small amount of retrograde flow. Examples of such closure members are described in U.S. Patent Application Publication No. 2008/0249612, the entire contents of which are hereby incorporated into this disclosure by reference.

Referring to FIGS. 5a, 5b, during antegrade fluid flow, fluid (e.g., blood) exerts pressure on the second side 62 of the single leaflet 54, urging the second edge 58 back across the fluid flow path 64 and forcing out fluid collected in the interior cone or pocket portion of the single leaflet 54. As the single leaflet 54 opens, the second edge 58 is forced out toward the body vessel wall to assume the open position 66 shown in FIGS. 5a, 5b, opening the implantable valve prosthesis and allowing antegrade fluid flow, or blood to flow in an antegrade direction.

Alternatively, in other embodiments, multicusp leaflet configurations may be utilized for the closure member. Multicusp leaflet configurations are known in the art; examples of suitable such structures are described in U.S. Patent Application Publication No. 2004/0260389, the entire contents of which are hereby incorporated into this disclosure by reference. The closure member can have multiple leaflets configured in such a manner to allow the leaflets to co-apt within the fluid flow path of the frame structure and graft member. The valve leaflets can have any suitable shape. In one embodiment, the valve leaflets include one or more edges attached to a support member and extend within the lumen. In certain embodiments, the valve leaflets have (n) edges and (n−1) edges of each valve leaflet preferably contact the graft member 18, where (n) is an integer equal to 2 or greater. In other embodiments, valve leaflets with (n) of 2, 3, or 4 are preferred, although valve leaflets with other shapes can also be used. In one embodiment, at least 2 edges of each valve leaflet are attached to the graft member 18, and at least one edge of each valve leaflet is a leaflet free edge that is not attached to the graft member 18.

One example of a multicusp leaflet is shown in FIG. 4. In this example, the graft member 18 has a bicusp leaflet closure member 20. The bicusp leaflet closure member 20 contains two leaflets 86, 88 positioned inside the frame structure.

Another example of a multicusp leaflet is shown in FIGS. 5a, 5b. In this example, a cross-sectional view of tricusp leaflet configuration is displayed. The tricusp leaflet configuration contains three leaflets 76, 78, 80 positioned inside the frame structure. The outer edges of the leaflets 76, 78, 80 are connected to the graft member 18. Also, each leaflet may be joined with the other leaflets at an edge points 82, extending from the graft member 18. Each leaflet also contains a free edge 84 that is movable between an open position 66 allowing antegrade flow, and a closed, or substantially closed, position 68 restricting retrograde flow.

In other embodiments, the closure member is a tubular valve or another kind of non-leaflet type valve structure. A non-limiting example of a tubular valve structure is described in U.S. patent Application Publication No. 2005/0085900, the entire contents of which are hereby incorporated into this disclosure by reference. Another example of a tubular valve structure is shown in FIGS. 7a and 7b. In this example, the first frame 14 and second frame 16 are independent of each other, connected by a graft member 18 having a closure member 20. The frame structure 12 and graft member 18 thereby form the intraluminally-placed valve prosthesis 10.

The graft member 18 and closure member 20 may be formed from one piece of the same material, or they may be formed from separate pieces that are held together by any number of techniques previously described. In FIGS. 7a and 7b, the closure member 20 is has a cone-shape formation and is connected to the graft member 18 by stitches 70.

The closure member 20 is oriented with the open end of the cone shape facing the direction of longitudinal retrograde fluid flow 94. Referring to FIG. 7a, when fluid flows through the body vessel in the retrograde direction 94, fluid pressure on the surface of the closure member 20 forces the movable edge of the closure member 20 to push up and seal against the wall of the graft member 18 and frame structure. The closure member quickly fills with the retrograde flowing fluid, preventing retrograde fluid flow from flowing through the implantable valve prosthesis. In certain embodiments, the closure member 20 may include "holes" or small openings 96 in the closure member 20, allowing a small amount of retrograde flow. This embodiment is described in detail in U.S. Pat. Publication Application No. 2008/0249612, the contents of which are herein incorporated by reference.

Referring to FIG. 7b, during antegrade fluid flow, fluid (e.g., blood) exerts pressure on the movable edge of the closure member 20, urging the movable edge to move across the lumen and create an opening 90 in the fluid flow path. As the closure member 20 opens, fluid is allowed to flow in the antegrade direction 92.

Figure 8:
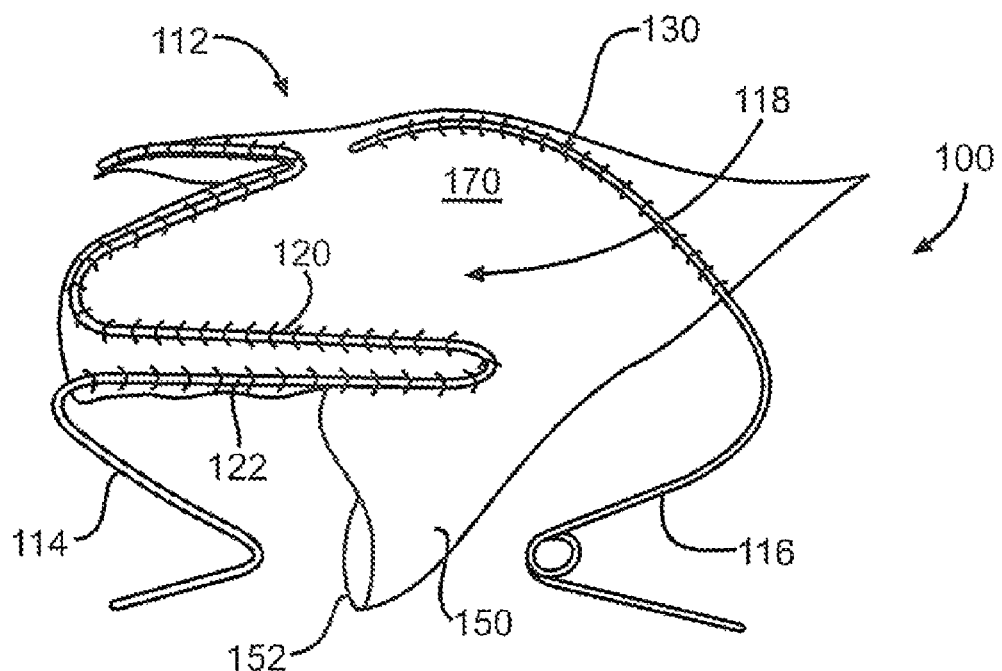
FIG. 8 is a side view of an implantable valve prosthesis according an exemplary embodiment.

FIG. 8 illustrates an implantable valve prosthesis 100 according to an exemplary embodiment. The valve device 100 includes a frame structure 112 having first 114 and second 116 independent frame elements. A bioprosthetic valve 118 is attached to the frame structure 112 by attachments to the independent frame elements 114, 116.

Each of the frame elements 114, 116 is a self-expandable support frame formed from a wire of a spring metal, such as stainless steel. The first frame element 114 defines a first serpentine path that extends around the circumference of the frame structure 112. The second frame element 116 defines a second serpentine path that also extends around the circumference of the frame structure 112. Each serpentine path includes straight strut portions that are interconnected by bends. One or both of the frame elements 114, 116 advantageously includes conventional structural features that facilitate anchoring, such as barbs, and structural features, such as radiopaque markers, that facilitate visualization of the valve device 100 in conventional or other medical visualization techniques, such as radiography, fluoroscopy, and other techniques. Furthermore, one or both of the frame elements 114, 116 can include coil structures, such as the safety pin members described above.

In the illustrated embodiment, the first frame element 114 includes first 120 and second 122 struts that are substantially straight and disposed substantially parallel to each other. This arrangement of struts 120, 122 is considered advantageous at least because it provides a degree of structural redundancy and gives a secondary attachment point for the bioprosthetic valve 118. A second set of substantially straight substantially parallel connector struts is disposed on the opposite side of the first frame member (not illustrated).

The second frame element 116 includes an elongate strut 130 that defines an outwardly-projecting curve. When the valve device 100 is implanted in a body vessel, the curve forces a part of the vessel wall outward, which defines a sinus at the point of implantation. This structural feature is considered advantageous at least because the provision of a sinus is believed to aid in the opening and closing of the bioprosthetic valve 118 by creating flow patterns that facilitate movement of the free edge 152 of the leaflet 150, which may enhance the overall performance of the valve device 100. It is believed to be advantageous to attach the contiguous wall portion 170 of the bioprosthetic valve 118 to the strut 130 defining the outwardly projecting curve. It is believed to be particularly advantageous to form a continuous attachment between the contiguous wall portion 170 and the strut 130 defining the outwardly projecting curve, such as by suturing along the length of the curve and/or strut 130, at least because this is expected to ensure a more complete definition of the sinus region in the valve device 100 and to enhance securement of the bioprosthetic valve 116 to the frame element 116.

Figure 9:
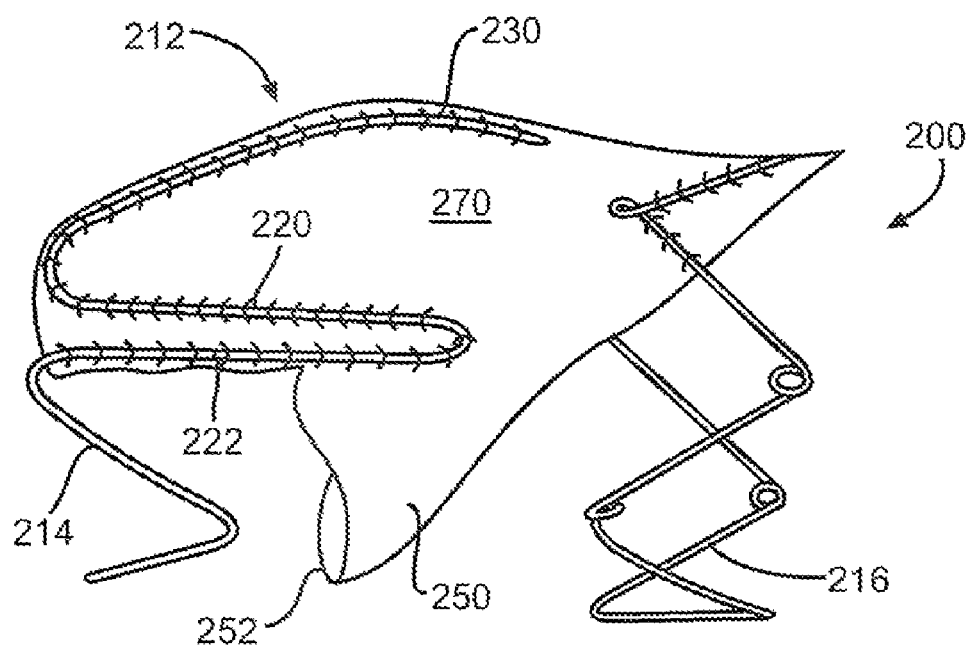
FIG. 9 is a side view of an implantable valve prosthesis according to another exemplary embodiment.

FIG. 9 illustrates an implantable valve prosthesis 200 according to another exemplary embodiment. The valve prosthesis 200 is similar to the valve prosthesis 100 illustrated in FIG. 8, except as described below. Thus, the valve prosthesis 200 includes a frame structure 212 having first 214 and second 216 independent frame elements. A bioprosthetic valve 218 is attached to the frame structure 212 by attachments to the independent frame elements 214, 216. Each of the frame elements 214, 216 is a self-expandable support frame. The first frame element 214 defines a first serpentine path that extends around the circumference of the frame structure 212. The second frame element 216 defines a second serpentine path that also extends around the circumference of the frame structure 212. Each serpentine path includes straight strut portions that are interconnected by bends.

The first frame element 214 includes first 220 and second 222 struts that are substantially straight and disposed substantially parallel to each other. A second set of substantially straight substantially parallel connector struts is disposed on the opposite side of the first frame member (not illustrated).

In this embodiment, the first frame element 214 defines the elongate strut 230 that defines an outwardly-projecting curve.

Figure 10:
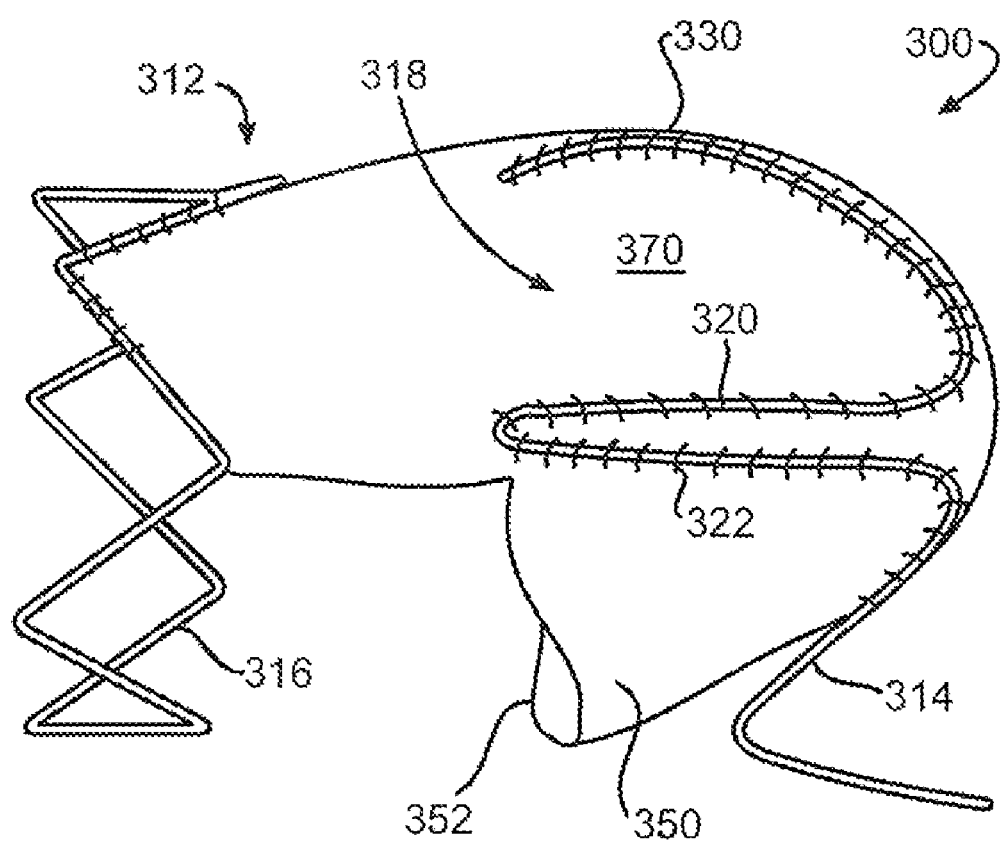
FIG. 10 is a side view of an implantable valve prosthesis according to another exemplary embodiment.

FIG. 10 illustrates an implantable valve prosthesis 300 according to another exemplary embodiment. The valve prosthesis 300 is similar to the valve prosthesis 200 illustrated in FIG. 9, except as described below. Thus, the valve prosthesis 300 includes a frame structure 312 having first 314 and second 316 independent frame elements. A bioprosthetic valve 316 is attached to the frame structure 312 by attachments to the independent frame elements 314, 316. Each of the frame elements 314, 316 is a self-expandable support frame. The first frame element 314 defines a first serpentine path that extends around the circumference of the frame structure 312. The second frame element 316 defines a second serpentine path that also extends around the circumference of the frame structure 312. Each serpentine path includes straight strut portions that are interconnected by bends.

The first frame element 314 includes first 320 and second 322 struts that are substantially straight and disposed substantially parallel to each other. A second set of substantially straight substantially parallel connector struts is disposed on the opposite side of the first frame member (not illustrated). The first frame element 314 defines the elongate strut 330 that defines an outwardly-projecting curve.

In this embodiment, the first frame element 314 is attached to the distal end of the graft member 318, which includes the valve leaflet 350, while the second frame element 316 is disposed at the proximal end of the graft member 318, which is spaced from the valve leaflet 350 along a lengthwise axis of the valve prosthesis 300. This arrangement is substantially opposite the arrangement illustrated in FIG. 9.

Figure 11A:
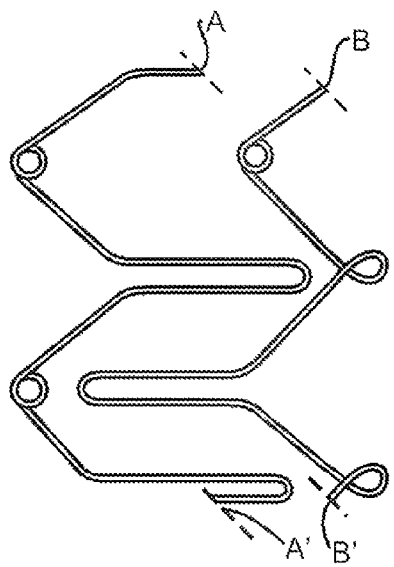
FIG. 11a is a flat plan view of an embodiment of the frame structure of an exemplary implantable valve prosthesis, wherein independent elements A-A' and B-B' can be circularized to form the three-dimensional frame structure.
Figure 11B:
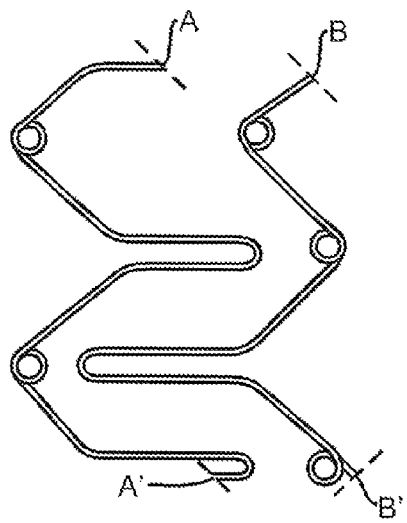
FIG. 11b is a flat plan view of an embodiment of the frame structure of an exemplary implantable valve prosthesis, wherein independent elements A-A' and B-B' can be circularized to form the three-dimensional frame structure.
Figure 11C:
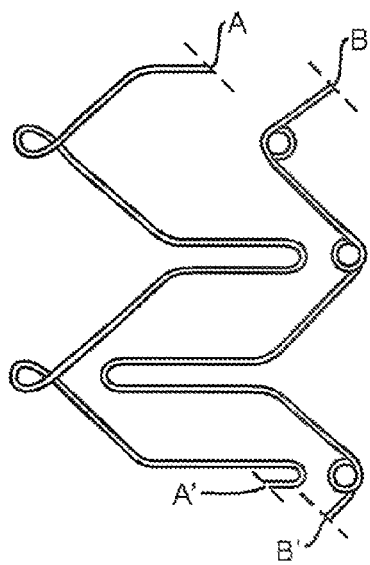
FIG. 11c is a flat plan view of an embodiment of the frame structure of an exemplary implantable valve prosthesis, wherein independent elements A-A' and B-B' can be circularized to form the three-dimensional frame structure.
Figure 11D:
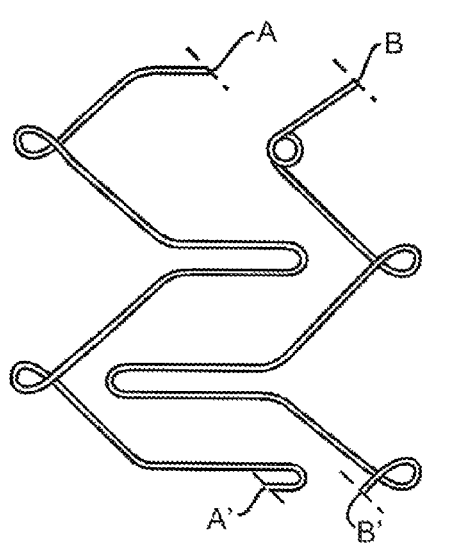
FIG. 11d is a flat plan view of an embodiment of the frame structure of an exemplary implantable valve prosthesis, wherein independent elements A-A' and B-B' can be circularized to form the three-dimensional frame structure.

Each of FIGS. 11A, 11B, 11C, and 11D illustrate a flat plan view of an embodiment of the frame structure of an exemplary implantable valve prosthesis, wherein independent frame elements A-A' and B-B' can be circularized to form a three-dimensional frame structure for inclusion in a valve prosthesis as described herein. The illustrated frame elements show various structural arrangements of loops that can be included in frame elements used in a valve prosthesis as described herein. All loops can extend in the same direction, as illustrated in FIG. 11A, or the loops of the different frame elements can extend in opposite directions, as illustrated in FIG. 11D. One or both frame elements can include loops that alternate in their direction of extension relative to the frame element and/or their direction of winding relative to the frame element, as illustrated in FIG. 11B and FIG. 11C.

Modifications and variations are possible without departing from the scope of the invention defined in the appended claims. More specifically, although some aspects are identified herein as preferred or particularly advantageous, it is contemplated that the scope of the invention is not necessarily limited to these preferred or advantageous aspects. This detailed description is illustrative and is not intended to limit the scope of the invention or the protection sought.

What is claimed is:

1. A valve prosthesis adapted for implantation in a body vessel and having a lengthwise axis, said valve prosthesis comprising:
    a first frame element defining a serpentine path comprising a series of substantially straight strut portions interconnected by bends;
    a second frame element defining a path that includes first and second substantially straight struts disposed substantially parallel to each other and third and fourth substantially straight struts disposed substantially parallel to each other, the first and second substantially straight struts disposed circumferentially opposite the third and fourth substantially straight struts with respect to said lengthwise axis;
    one of the first and second frame elements further comprising an elongate strut that defines an outwardly-projecting curve with respect to said lengthwise axis, the outwardly-projecting curve adapted to define a sinus in said body vessel when said valve prosthesis is implanted therein; and
    a graft member attached to the first frame element and the second frame element, the graft member comprising a closure member adapted to move between a first position that allows fluid flow through said implantable valve prosthesis in a first, antegrade direction and a second position that restricts fluid flow through said implantable valve prosthesis in a second, retrograde direction;
    wherein the first and second frame elements are connected to each other only by attachments of the graft member to the first and second frame elements.

2. The valve prosthesis of claim 1, wherein the first frame has a first frame expanded diameter and the second frame has a second frame expanded diameter; and
    wherein the first frame expanded diameter is different than the second frame expanded diameter.

3. The valve prosthesis of claim 1, wherein the graft member is a flexible material selected from the group consisting of polymeric material, collagen, extracellular matrix material, and mixtures thereof.

4. The valve prosthesis of claim 3, wherein the polymeric material is a polyester.

5. The valve prosthesis of claim 3, wherein the extracellular matrix material is selected from the group consisting of: small intestine submucosa, stomach submucosa, uterine submucosa, urinary bladder submucosa, tissue mucosa, basement membrane materials, renal capsule, serosa, peritoneum, dura matter, pericardium, elastin, elastin-like polypeptides, and mixtures thereof.

6. The valve prosthesis of claim 1, wherein one of the first and second frame elements is constructed from a shape-memory alloy material selected from the group consisting of: Ni—Ti, Au—Cd, Cu—Zn, In—Ti, Cu—Zn—Al, Ti—Nb, Au—Cu—Zn, Cu—Zn—Sn, Cu—Zn—Si, Cu—Al—Ni, Ag—Cd, Cu—Sn, Cu—Zn—Ga, Ni—Al, Fe—Pt, U—Nb, Ti—Pd—Ni, Fe—Mn—Si, Ni—Ti—Cr, and alloy mixtures thereof.

7. The valve prosthesis of claim 1, wherein one of the first and second frame elements is constructed from a material selected from the group consisting of: tantalum, stainless steel, titanium, niobium, gold, platinum, cobalt, and mixtures thereof.

8. The valve prosthesis of claim 1, wherein one of the first and second frame elements is constructed from a polymer selected from the group consisting of polyethylene, polypropylene, polyisobutylene, poly(alpha olefin), alkyl acrylates, polymethyl acrylate, polymethyl methacrylate, parylene, ethyl vinyl acetate; polyethylene-co-vinyl acetate, polyesters, polycarbonates, polyoxaesters, polyanhydrides, polyamino acids, polyphosphazenes, phosphorylcholine, phosphatidylcholine, hydrogels, polydioxanone, poly(DTE carbonate, fibrin, collagens, extracellular matrix materials, dextrans, polysaccharides, hyaluronic acid, bioabsorbable polymers, and mixtures thereof.

9. The valve prosthesis of claim 1, wherein the graft member comprises at least one leaflet and a contiguous wall portion harvested from a natural valve.

10. The valve prosthesis of claim 9, wherein the contiguous wall portion is attached to the elongate strut that defines an outwardly-projecting curve.

11. The valve prosthesis of claim 10, wherein the contiguous wall portion is attached to the elongate strut that defines an outwardly-projecting curve by a continuous attachment between the contiguous wall portion and the strut that defines an outwardly-projecting curve.

12. The valve prosthesis of claim 11, wherein the strut that defines an outwardly-projecting curve has a strut length and wherein the continuous attachment comprises sutures attaching the contiguous wall portion to the strut that defines an outwardly-projecting curve along the strut length.

13. The valve prosthesis of claim 11, wherein the outwardly-projecting curve has a curve length and wherein the continuous attachment comprises sutures attaching the contiguous wall portion to the strut that defines an outwardly-projecting curve along the curve length.

14. The valve prosthesis of claim 1, wherein the second frame element comprises the elongate strut that defines an outwardly-projecting curve.

15. A valve prosthesis adapted for implantation in a body vessel and having a lengthwise axis, said valve prosthesis comprising:
    a first frame element defining a serpentine path comprising a series of substantially straight strut portions interconnected by bends;
    a second frame element defining a path that includes first and second substantially straight struts disposed substantially parallel to each other and third and fourth substantially straight struts disposed substantially parallel to each other, the first and second substantially straight struts disposed circumferentially opposite the third and fourth substantially straight struts with respect to said lengthwise axis;

the second frame element further comprising an elongate strut that defines an outwardly-projecting curve with respect to said lengthwise axis, the elongate strut disposed circumferentially between the first and second substantially straight struts and the third and fourth substantially straight struts with respect to said lengthwise axis, the outwardly-projecting curve adapted to define a sinus in said body vessel when said valve prosthesis is implanted therein; and a graft member attached to the first frame element and the second frame element, the graft member comprising a closure member adapted to move between a first position that allows fluid flow through said implantable valve prosthesis in a first, antegrade direction and a second position that restricts fluid flow through said implantable valve prosthesis in a second, retrograde direction;

wherein the first and second frame elements are connected to each other only by attachments of the graft member to the first and second frame elements.

16. The valve prosthesis of claim 15, wherein the graft member comprises at least one leaflet and a contiguous wall portion harvested from a natural valve.

17. A valve prosthesis adapted for implantation in a body vessel and having a lengthwise axis, said valve prosthesis comprising:

a first frame element defining a serpentine path comprising a series of substantially straight strut portions interconnected by bends;

a second frame element independent of the first frame element and defining a path that includes first and second substantially straight struts disposed substantially parallel to each other and third and fourth substantially straight struts disposed substantially parallel to each other, the first and second substantially straight struts disposed circumferentially opposite the third and fourth substantially straight struts with respect to said lengthwise axis;

the second frame element further comprising an elongate strut that defines an outwardly-projecting curve with respect to said lengthwise axis, the elongate strut disposed circumferentially between the first and second substantially straight struts and the third and fourth substantially straight struts with respect to said lengthwise axis, the outwardly-projecting curve adapted to define a sinus in said body vessel when said valve prosthesis is implanted therein; and a graft member attached to the first frame element and the second frame element, the graft member comprising at least one leaflet and a contiguous wall portion harvested from a natural valve, the contiguous wall portion attached to the elongate strut that defines an outwardly-projecting curve;

wherein the first and second frame elements are connected to each other only by attachments of the graft member to the first and second frame elements.

* * * * *